(12) United States Patent
Haar et al.

(10) Patent No.: US 6,986,754 B2
(45) Date of Patent: Jan. 17, 2006

(54) NEEDLELESS HYPODERMIC INJECTION SYSTEM, APPLICATION DEVICE AND MEDICATION CARTRIDGE THEREFOR

(75) Inventors: Hans-Peter Haar, Wiesloch (DE); George Bevan Kirby Meacham, Shaker Heights, OH (US); Konrad Joseph Popp, Augsburg (DE); Otto Bruntrup, Munich (DE); Ulrich Josef Riemensperger, Edenried-Aichach (DE); Guenter Franz Ihle, Mauer (DE); Bruno Robert Thös, Quierschied (DE); Hans List, Hesseneck (DE); Dirk Bandau, Ottersheim (DE); Horst Engelhardt, Neuhofen (DE); Christian Gliewe, Lampertheim (DE)

(73) Assignee: Roche Diagnostics GmbH, Mannheim (DE)

( * ) Notice: Subject to any disclaimer, the term of this patent is extended or adjusted under 35 U.S.C. 154(b) by 678 days.

(21) Appl. No.: 10/101,400

(22) Filed: Mar. 19, 2002

(65) Prior Publication Data

US 2002/0169412 A1 Nov. 14, 2002

Related U.S. Application Data

(60) Provisional application No. 60/278,042, filed on Mar. 22, 2001.

(51) Int. Cl.
    *A61M 5/30* (2006.01)

(52) U.S. Cl. ....................................................... 604/70
(58) Field of Classification Search ............. 604/68–72, 604/131, 140, 143
    See application file for complete search history.

(56) References Cited

U.S. PATENT DOCUMENTS

| | | | | |
|---|---|---|---|---|
| 3,335,722 A | * | 8/1967 | Lowry et al. | 604/69 |
| 3,802,430 A | * | 4/1974 | Schwebel et al. | 604/69 |
| 4,089,334 A | * | 5/1978 | Schwebel et al. | 604/69 |

(Continued)

FOREIGN PATENT DOCUMENTS

| | | |
|---|---|---|
| EP | 1 013 297 | 6/2000 |
| FR | 2 796 291 | 1/2001 |
| WO | WO 98 13085 | 4/1998 |
| WO | WO 98/31409 A2 | 7/1998 |
| WO | WO 01 05451 | 1/2001 |

*Primary Examiner*—Sharon Kennedy
(74) *Attorney, Agent, or Firm*—George W. Johnston; Patricia S. Rocha-Tramaloni; Kimberly J. Prior

(57) ABSTRACT

A needleless hypodermic injection system for injecting a liquid medication, which system comprises a disposable cartridge which contains a medication and which includes a propellant and an igniter, and a reusable application device which comprises a pressure chamber for receiving the medication cartridge, actuation means including an ignition system and means for ensuring reliability and safety of the system. The reusable application device comprises:

(a) a housing including a fist housing section and a second housing section which are adapted to be assembled together by a screwing operation, the first housing section comprising a front part having an injection outlet and a chamber adapted to receive a the cartridge contains the medication to be injected and also contains a propellant and an igniter, and
(b) means for selectively activating said igniter of said cartridge when predetermined conditions are fulfilled.

17 Claims, 7 Drawing Sheets

U.S. PATENT DOCUMENTS

| | | |
|---|---|---|
| 4,680,027 A | 7/1987 | Parsons et al. |
| 5,080,648 A | 1/1992 | D'Antonio |
| 5,383,851 A | 1/1995 | McKinnon, Jr. et al. |
| 5,782,802 A | 7/1998 | Landau |
| 6,096,002 A | 8/2000 | Landau |
| 6,171,276 B1 | 1/2001 | Lippe et al. |
| 6,610,028 B1 | 8/2003 | Alexandre et al. |
| 2002/0156418 A1 * | 10/2002 | Gonnelli et al. .............. 604/69 |

* cited by examiner

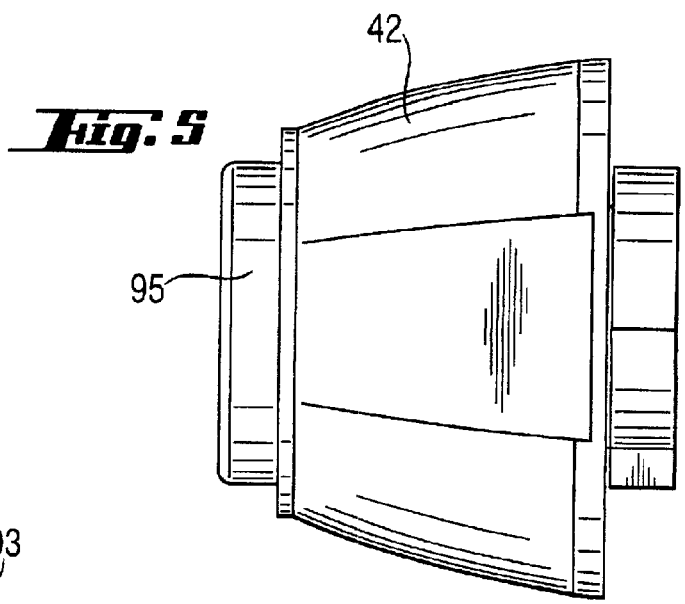
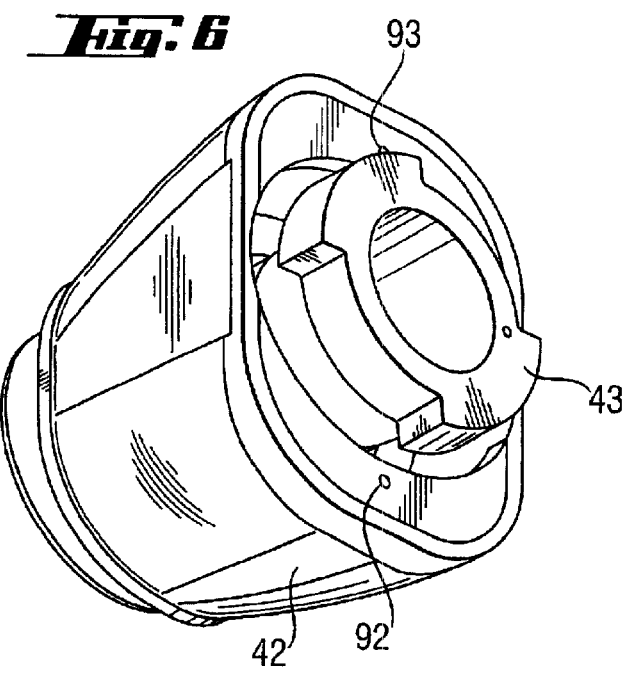
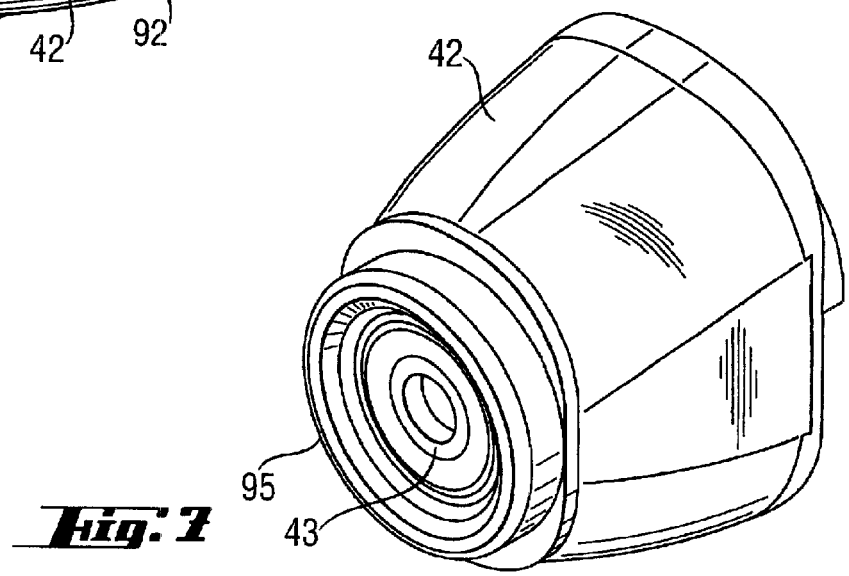

NEEDLELESS HYPODERMIC INJECTION SYSTEM, APPLICATION DEVICE AND MEDICATION CARTRIDGE THEREFOR

FIELD OF THE INVENTION

The invention concerns a needleless hypodermic injection system for injecting a liquid medication.

The invention also concerns a reusable application device which is a first part of such a system.

The invention further concerns a disposable medication cartridge which is a second part of such a system.

BACKGROUND OF THE INVENTION

Prior art systems and devices of the above mentioned kind have important disadvantages. They have a complex structure and are therefore not easy to assemble and to use, in particular for patients which have some handicaps or are not in full possession of their handling capabilities. Moreover they lack reliable means for preventing accidental release of injections and their negative consequences, e.g. loss of expensive medications and possible injures inflicted to the user.

The main aim of the instant invention is therefore to provide a system an application device, and a medication cartridge of the above mentioned kind with which the above mentioned drawbacks can be eliminated or at least substantially reduced.

SUMMARY OF THE INVENTION

According to a first aspect of the invention the above mentioned aim is attained with a needleless hypodermic injection system for injecting a liquid medication, which system comprises:

(a) a disposable cartridge which contains a medication and which includes a propellant and an igniter, and (b) a reusable application device which comprises a pressure chamber for receiving said cartridge, and actuation means including an ignition system and means for ensuring reliability and safety of the system.

According to a second aspect of the invention the above mentioned aim is attained with a reusable application device for a needleless hypodermic injection system for injecting a liquid medication contained in a cartridge inserted into said application device, said application device comprising (a) a housing including a first section and a second section which are adapted to be connected with each other to form a housing assembly, said first housing section comprising a chamber for receiving a cartridge containing a medication unit which contains a liquid medication, said first housing section having a symmetry axis which extends along its length and a front part having an outer contact surface which is adapted to be applied on a skin surface, said contact surface having an opening through which liquid medication ejected from said cartridge can pass and be injected through said skin surface, (b) ejection means for causing ejection of said liquid medication contained in said cartridge in order to perform an injection, a first part of said ejection means being contained in said cartridge and a second part of said ejection means being contained in said second housing section, c) assembly detecting means which reach a first predetermined state when said first housing section is properly and completely assembled with said second housing section to form said housing assembly, said assembly detecting means being located within said housing assembly, d) position detecting means which are located in part within said first housing section and in part in said second housing section, said position detecting means reaching a second predetermined state when the following conditions are simultaneously satisfied by the relative position of said housing assembly with respect to said skin surface, d.2) said contact surface of said first section exerts a predetermined pressure on said skin surface, the distribution of said pressure over the area of said contact surface being substantially uniform, and d.3) said symmetry axis of said first section is positioned substantially normal to said skin surface, and e) actuator means for activating said ejection means, said actuator means being normally disabled and becoming operable only upon being enabled by a combination of predetermined effects provided by said assembly detecting means after they reach said first predetermined state, and said position detecting means when they reach said second predetermined state.

According to a third aspect of the invention the above mentioned aim is attained with a reusable application device for a needleless hypodermic injection system for injecting a liquid medication contained in a cartridge inserted into said application device, said cartridge containing a propellant adapted to be ignited by application of electrical energy to two electrical contacts which are part of said cartridge, said application device comprising a) a housing including a first section and a second section, each of these sections having a length axis and said first and second housing sections being adapted to be connected with each other to form a housing assembly, said housing assembly being so configured and dimensioned that it is adapted to be held by a user with one hand, b) said first housing section comprising a chamber for receiving a cartridge containing a liquid medication, said first section having an outer contact surface which is adapted to be applied on a skin surface through which an injection is to be applied, c) said second housing section containing electrical means for causing ignition of a propellant contained in a cartridge arranged in said chamber of said first housing section and actuator means for activating said electrical means, and d) position detecting means for detecting whether said contact surface of said first section exerts a predetermined pressure on said skin surface and whether at the same time said length axis of said first section is positioned substantially normal to said skin surface, the distribution of said pressure over the area of said contact surface being substantially uniform, said means for detecting enabling said actuator means when the latter conditions are satisfied.

According to a fourth aspect of the invention the above mentioned aim is attained with a reusable application device for a needleless hypodermic injection system for injecting a liquid medication, which application device comprises:

(a) a housing including a fist housing section and a second housing section which are adapted to be assembled together by a screwing operation, said first housing section comprising a front part having an injection outlet and a chamber adapted to receive a cartridge containing a medication unit which contains the medication to be injected, a propellant, and an igniter, and (b) means for selectively activating said igniter of said cartridge when predetermined conditions are fulfilled.

According to a fifth aspect of the invention the above mentioned aim is attained with a medication cartridge for a needleless hypodermic injection system for injecting a liquid medication, said cartridge comprising a housing adapted to contain:

(a) a first chamber containing a medication unit configured and dimensioned to store a volume of liquid to be injected, said medication unit having a first region and a second region that are in liquid communication with each other, said first region being deformable and said second region having an injection outlet, and (b) a second chamber containing a propellant, said first chamber being divided by an elastic barrier in two zones, a first zone containing said medication unit and a second zone which is communication with said second chamber, so that upon ignition of the propellant in the second chamber gas generated thereby expands into said second zone of said first chamber, exerts pressure on and deforms said barrier which in turn transfers that pressure to and deforms said deformable first region of said medication unit and thereby causes ejection of said medication through said injection outlet, and (c) means for mechanically setting the volume available within said cartridge for gas said expansion, so that said volume has a selected predetermined size.

The main advantages attained with the invention are as follows:

Injections can only be performed when plurality of predetermined necessary conditions for a correct injection are satisfied. Therefore, the risk of accidentally released injections and their negative consequences, e.g. loss of expensive medications and possible injure of user, are substantially reduced.

A device and a system according to the invention are easy, safe and comfortable to use, so that they can be assembled and used by patients or other persons without any training or special instructions.

The manufacturing cost of a device and a system according to the invention is not higher than prior art devices for the same purpose.

BRIEF DESCRIPTION OF THE DRAWINGS

The subject invention will now be described in terms of its preferred embodiments with reference to the accompanying drawings. These embodiments are set forth to aid the understanding of the invention, but are not to be construed as limiting.

FIG. 5 shows a side view of the nose section 42 of an application device of the kind shown by FIG. 4.

FIG. 6 shows a first perspective view of the nose section 42 shown by FIG. 5.

FIG. 7 shows a second perspective view of the nose section 42 shown by FIG. 5.

DETAILED DESCRIPTION OF PREFERRED EMBODIMENTS

According to the invention a reusable application device is used as part of a needleless hypodermic injection system for injecting a liquid medication contained in a cartridge inserted into said application device.

Medication Cartridge Assembly

Figure 1:
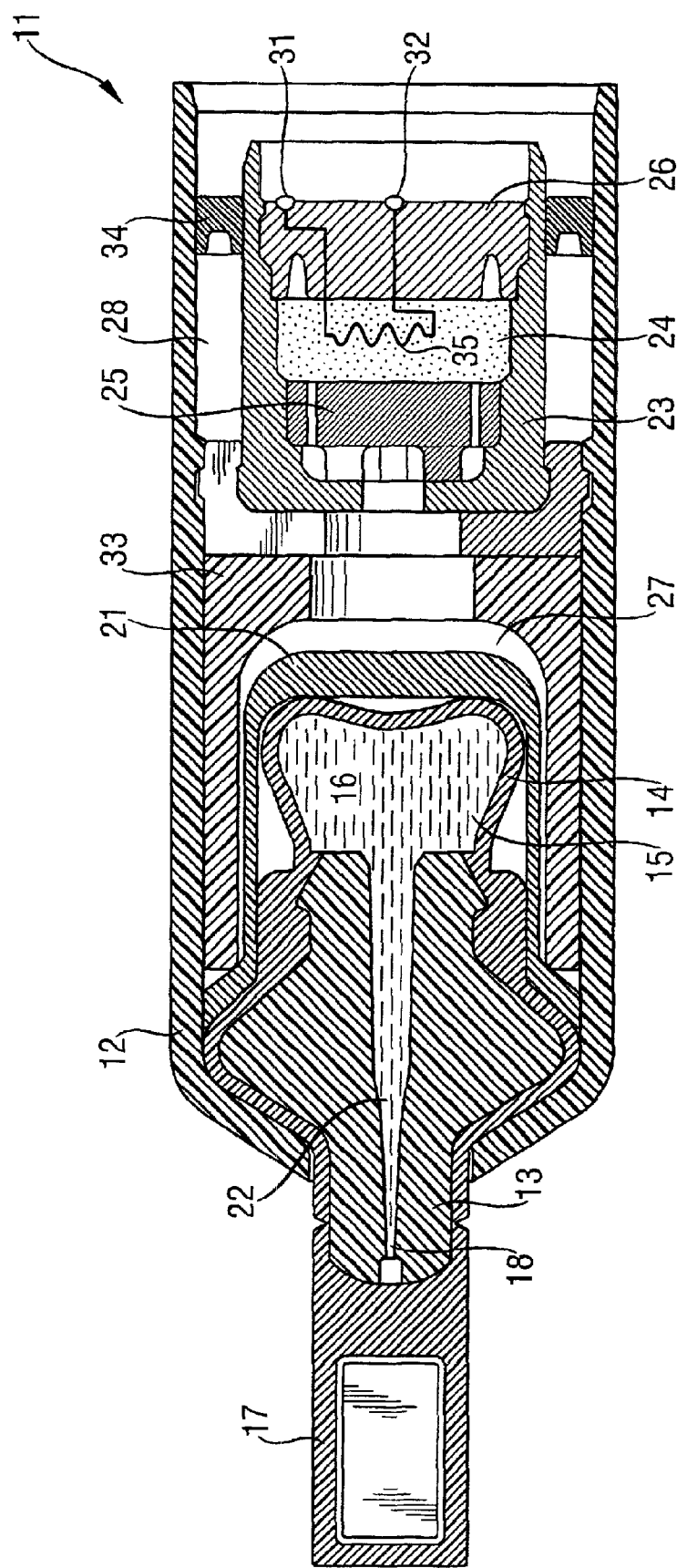
FIG. 1 shows a schematic cross sectional view of a basic structure of a medication cartridge 11 used in a needleless injection system according to the invention.

As shown by FIG. 1 a medication cartridge assembly 11 according to the invention comprises components described hereinafter.

A cartridge shell 12 made e.g. of a plastic material contains among other components a sealed medication module which comprises a nozzle body 13 and a flexible container wall 14 that hermetically encloses a portion of the nozzle and forms a reservoir 15 for a liquid medication 16 stored in the sealed medication module. This sealed module including liquid medication 16 stored therein is manufactured under sterile conditions.

A part of the container wall 14 forms a break-off protective cap 17 that covers a jet orifice 18 of nozzle body 13. Cap 17 is removed by the user just prior to use.

An envelope 21 made e.g. of rubber surrounds the flexible container wall 14 and serves as a protective barrier. Envelope 21 protects flexible wall 14 from direct hot gas contact, and prevents hot gas from entering a fluid channel 22 within nozzle body 13 and jet orifice 18 of nozzle body 13 even in the event of a break in the flexible container wall 14. Envelope 21 also forms a gas seal between the cartridge shell 12 and the medication module containing the liquid medication 16.

Cartridge shell 12 unifies the components contained therein and contains also gas generated within cartridge shell 12 by a gas generator contained therein during actuation. The wall of cartridge shell 12 may be relatively thin since it transfers the gas pressure forces generated within cartridge shell 12 to a surrounding high strength chamber that is part of a reusable actuation device described hereinafter.

Injection energy is provided by a gas generator located in the rear part of cartridge shell 12. This gas generator is a subassembly consisting of a metal gas generator body 23 which has a propellant containing chamber 24 located between an outlet orifice plate 25 and a closure plug or closure plate 26. When the gas generator is actuated in order to provide the energy necessary for performing an injection of the liquid medication, a propellant contained in propellant chamber 24 is ignited by an electrically heated wire and produces hot gas that flows to gas pressure chamber 27 surrounding envelope 21, flexible container wall 14 and medication reservoir 15 and an annular co-volume 28 the size of which is defined by the axial position of a co-volume seal ring 34.

Heating wire adapted to be electrically heated is arranged within propellant chamber 24. This heating wire is electrically connected with ignition contacts 31, 32 arranged in closure plate. When the medication cartridge assembly is properly positioned within the reusable application device ignition contacts 31, 32 engage corresponding electrical contacts which are part of the application device described hereinafter. Electric power is deliverable to the heating wire 35 (shown in FIG. 11) arranged within propellant chamber 24 through the latter contacts and ignition contacts 31, 32 engaged therewith.

Cartridge shell 12 further contains an internal support 33 which e.g. a structure made of a plastic material that snaps into cartridge shell 12 and holds the above described sealed medication module and the gas generator in position. When cartridge assembly 11 is inserted into and properly positioned within an application device described hereinafter in order to perform an injection, a part of this application device pushes on the rear of cartridge assembly 11 and clamps the closure plate 26 of the gas generator, internal support 33, envelope 21 and the above described sealed medication module into the nose of cartridge shell 12. Cartridge assembly 11 remains so clamped during actuation thereof by the application device for performing the injection. This clamping action on cartridge assembly 11 assures that this assembly is hermetically sealed to prevent hot gas leakage around jet orifice 18 of nozzle body 13.

When a cartridge assembly is actuated by the application device, pressure exerted by gas surrounding a part of the sealed medication module within cartridge shell 12 is transmitted to liquid medication 16 contained in the sealed medication module through flexible container wall 14. The pressure exerted in this way on the liquid medication causes a collapsing of flexible container wall 14 and this drives the liquid medication through jet orifice 18 at high velocity. Peak pressure, up to 300 bar, occurs at the beginning of the injection and forces a jet of liquid medication to penetrate through a skin layer and thereby form a fluid delivery channel into the subcutaneous tissue. The pressure then drops to about 100 bar to complete the medication injection through the so formed fluid delivery channel.

Ease of jet penetration varies between patients or between injection sites on the same patient. The initial peak injection pressure is therefore adjusted to control the jet penetration force to an appropriate value. This adjustment is effected by positioning co-volume seal ring 34 at a suitable axial position with respect to cartridge shell 12 in order to set the value of the annular co-volume 28.

Increasing co-volume 28 increases the expansion volume of the gas generated and delivered by the gas generator and reduces the initial peak pressure to a lower value. A co-volume setting ring 48 that is part of the application device described hereinafter slides into the rear of cartridge 11 during loading of cartridge 11 into the application device, brings co-volume seal ring 34 into a selected position and holds this ring in this position.

A cartridge assembly 11 clamped into the actuation device described hereinafter is a hermetically sealed assembly, and retains as much as 100 bars pressure after actuation. The application device must therefore release the clamping force in a controlled way and allow that the gas pressure within cartridge 11 forces closure plug 26 of the gas generator out to break the seal with the gas generator body 23 and vent the gas. This controlled pressure release makes it easy to open the application device after it is used to perform an injection and prevents that the amount of pressure remaining in the cartridge after an injection may cause an undesirable forceful opening of the application device that may cause an injury to a user of the device.

Structure of an Application Device According to the Invention

The above described characteristics of cartridge assembly 11 define the basic functional requirements the application device has to satisfy. Additional requirements ensure safe and easy operation of the application device.

The force a user has to apply for loading a cartridge 11 into an application device and the force a user has to apply for removing a cartridge 11 from the application device after use for performing an injection must be low enough to allow easy and sure operation of the application device by ill or elderly patients.

Actuation of the application device must not be possible unless the device is fully closed and locked. Otherwise partial engagement of the locking mechanism might lead to failure and possible injury caused by the high pressure created during an injection operation.

To ensure that actuation of the application device is not possible unless the device is fully closed and locked, operation of an application device according to the invention requires that the nose part of the application device is pressed uniformly and with a predetermined force against the skin surface to be injected before actuation of the application device is enabled. Main objectives of this security measure are to prevent accidental actuation resulting in ejection of a liquid jet that might cause eye injury and also to prevent wasted injections due to premature actuation of the application device before the nose part thereof is properly pressed against the skin surface at the injection site.

The outer surface of the application device should riot have any sharp edges or pinch points and the design of the application device has to satisfy ergonomic requirements.

The shape of the application device has to be well adapted to the function it has to perform and therefore the procedures for loading and unloading a cartridge 11 into the application device and for actuating the application device should be so obviously and intuitively clear to the user that a minimum of user instruction is necessary to ensure proper use of the application device.

Moreover, the application device and in particular the area around the cartridge nozzle that contacts the skin during the injection should be adapted to be easily cleaned.

The injection system formed by cartridge 11 and the application device described hereinafter should be fail-safe and resistant to tampering. Any faults in the device should result in failure of device actuation rather than in an unexpected or dangerous actuation. The design of the latter injection system should be such that it discourages a "clever" person from modifying or tricking the device so that it operates improperly.

The application device described hereinafter meets the requirements outlined above.

Figure 2:
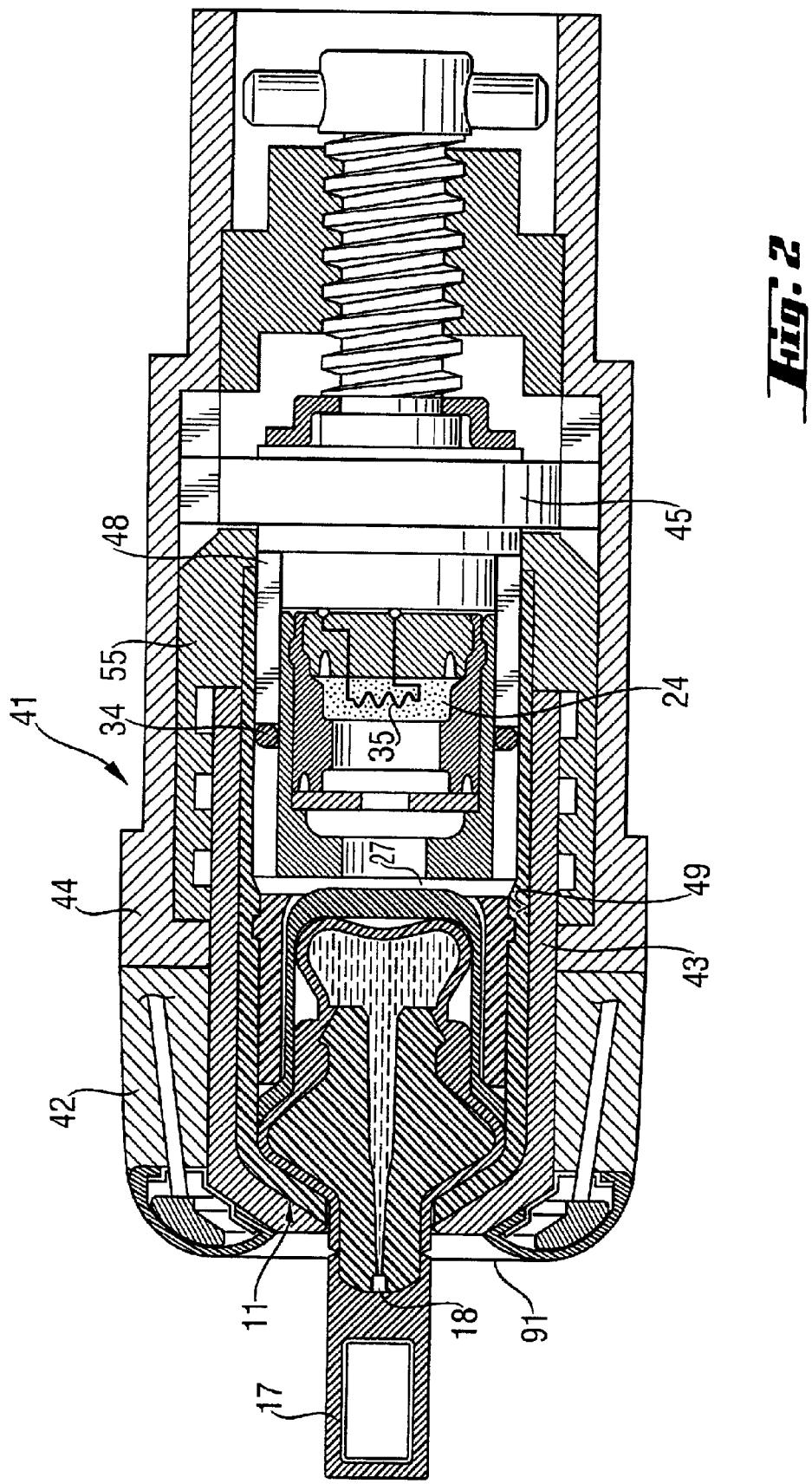
FIG. 2 shows a schematic cross sectional view of the basic structure of an application device according to the invention including a representation of a medication cartridge 11 according to FIG. 1.

As shown by FIG. 2, an application device 41 according to the invention comprises two sections: a nose section 42 which comprises a pressure chamber 49 defined by the interior of a shell 43 and adapted for receiving a cartridge assembly 11, and a base section 44 which comprises among other components a breech block 45 and an electrical ignition system (not shown in FIG. 2).

Nose section 42 and a base section 44 are assembled in two steps. In a first step a cartridge 11 is inserted into pressure chamber 49 of nose section 42 and after that nose section 42 and the cartridge 11 inserted thereinto are mechanically connected to base section 44. For this purpose, nose section 42 and base section 44 are twisted with respect to each other ¼ turn to provide engagement of a set of locking lugs.

In a second step nose section 42 is twisted of about one turn with respect to base section 44 for tightening a screw mechanism that clamps cartridge assembly 11 with a required preload of e.g. 200 Newton. At this point application device 41 is ready for performing an injection. For this purpose, the user removes break-off protective cap 17 from cartridge 11, presses jet orifice 18 of nozzle body 13 against a skin surface at the injection site, and then presses an actuation switch to release an injection.

Interlocks prevent actuation of the application device if it is not fully closed and if the skin contact surface of its nose section 42 is not uniformly pressed against the skin surface.

A spent cartridge is removed by reversing the loading process. For this purpose, nose section 42 is twisted of about one turn with respect to base section 44 to release the clamp screw mechanism and vent the residual cartridge gas pressure. The locking lugs are then disengaged by a further ¼ turn, and nose section 42 and base section 44 are separated from each other so that the spent cartridge may be removed and discarded.

Application device 41 is a tightly integrated system that comprises the following subsystems:

Pressure Chamber and Lock

Pressure chamber 49 and a lock which includes the above mentioned breech block are a set of mechanical components that enclose and contain a cartridge assembly 11 during a high-pressure injection.

Housing

A housing encloses and supports the other subsystems which form part of an application device according to the invention. This housing also forms the surfaces the user grips to administer injections and to open and close the application device for loading, respectively unloading of a cartridge 11.

Electric Ignition System

An electric ignition system includes a battery, an actuation switch, safety interlock switches and electrical connection leads. The electrical ignition system supplies electric current to the ignition contacts 31, 32 of cartridge 11 and thereby to ignition wire 35 (see FIG. 11) to start an injection process when the user presses the actuation switch.

Object Sensor

An object sensor comprises a mechanical structure surrounding jet orifice 18 of nozzle body 13 of cartridge 11. This mechanical structure comprises a skin contact surface of nose section 42. Two diametrically opposite places of this skin contact surface must be pressed against the injection site in order to enable application device 41 to actuate a cartridge 11 which has been loaded into application device 41.

The following sections describe each of the above mentioned subsystems in detail.

Pressure Chamber and Lock Mechanism

Figure 3:
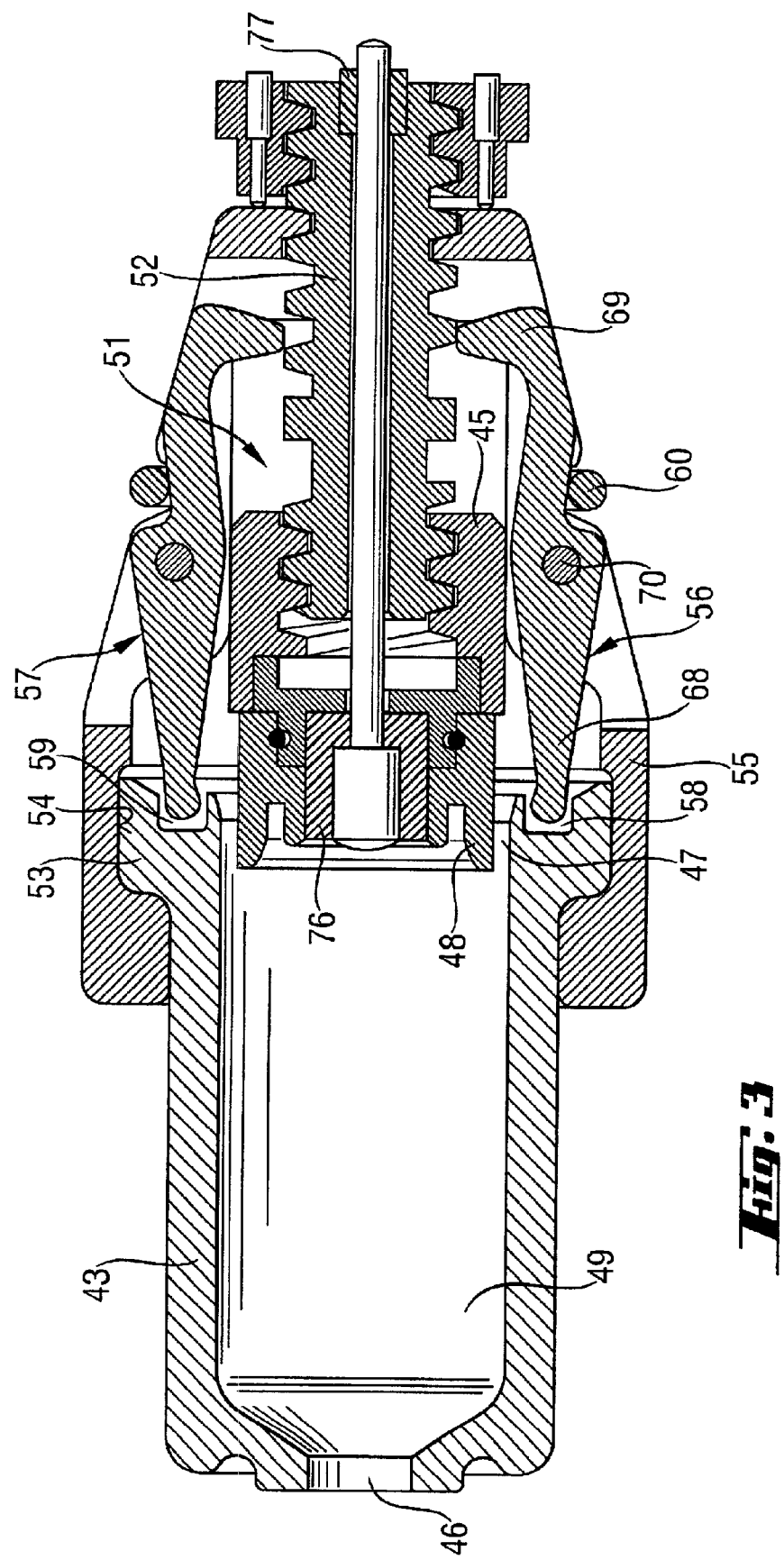
FIG. 3 shows a schematic cross sectional view of the pressure chamber and locking means which are part of the application device according to FIG. 2 and which are adapted to enclose and contain a medication cartridge 11 of the type shown by FIG. 1 during a high-pressure injection.

FIG. 3 shows a general arrangement of a pressure chamber 49 and a lock mechanism 51. Pressure chamber 49 is the interior of a generally cylindrical shell 43 with a reduced diameter opening 46 at one end and a full diameter opening 47 at the other end. The shell 43 of pressure chamber 49 is manufactured from high strength steel and dimensioned such that it will withstand about 900 bar internal pressure (that is three times a 300 bar maximum working pressure) without damage.

Lock mechanism 51 is part of a mechanical structure contained in and carried by base section 44. In order to load a new cartridge into the application device or to unload an spent cartridge from the application device, nose section 42 and base section 44 are disassembled as described above in order to separate the shell 43 of pressure chamber 49 from lock mechanism 51.

When cartridge 11 is inserted into pressure chamber 49 break-off protective cap 17 and the outer end of nozzle body 13 extend through the reduced diameter opening 46 of the shell 43 of pressure chamber 49. The shell 43 of pressure chamber 49 has a clearance fit with respect to cartridge shell 12. During an injection process the internal pressure within cartridge shell 12 expands it elastically and its outer wall contacts the internal surface of the shell 43 of pressure chamber 49, thereby transfers the pressure load to the shell 43 of pressure chamber 49 during the injection process, and limits the mechanical stress on cartridge shell 12. After an injection, the residual pressure in cartridge shell is released by venting (as described above) and cartridge shell elastically contracts. This restores the clearance fit of cartridge shell 12 with respect to the shell 43 of pressure chamber 49 and this allows easy removal of a used cartridge. Nozzle body 13 of cartridge 11 has sufficient strength to bridge the reduced diameter opening 46 and withstand the internal pressure in cartridge 11 during an injection process.

Full diameter opening 47 of the shell 43 of pressure chamber 49 is closed when shell 43 is engaged with lock mechanism 51. Lock mechanism 51 has several functions. A first function of lock mechanism 51 is that it locks to the shell 43 of pressure chamber 49 and carries the axial pressure force (which is a function of the cartridge internal diameter and the gas pressure) which tends to separate lock mechanism 51 from the shell 43 of pressure chamber 49. A second function of lock mechanism 51 is that it carries the ignition contacts of the application device that engage the ignition contacts 31, 32 of cartridge 11. A third function of lock mechanism 51 is that it carries an interchangeable co-volume setting ring which serves for setting the axial position of the co-volume seal ring 34 in cartridge 11. A fourth function of lock mechanism 51 is that it comprises a clamp screw 52 that allows the user to apply the necessary clamping force on cartridge 11 prior to actuation thereof, and to release the residual pressure in cartridge 11 in a slow and controlled way after an injection process. A fifth function of lock mechanism 51 is that it contains a mechanical interlock that assures that locking lugs are fully engaged before clamp screw 52 can be turned to prepare and bring the system composed by the application device and cartridge 11 to a state that allows actuation of cartridge 11 by the application device. Each of these functions is described in more detail in the following sections.

A pair of male locking lugs 53 on the shell 43 of pressure chamber 49 engage female pockets 54 in a receiver ring 55 of lock mechanism 51 to form a structural connection. The user makes this connection by inserting locking lugs 53 into receiver ring 55 with an axial motion, and then rotating the shell 43 of pressure chamber 49 ¼ turn with respect to receiver ring 55 to engage locking lugs 53 with female pockets 54. This type of connection is widely used in firearms and hose couplings because of its strength and reliability.

After locking lugs 53 are fully engaged with female pockets 54, clamp screw 52 is turned to push breechblock 45 into cartridge 11. Clamp screw 52, the shell 43 of pressure chamber 49, receiver ring 55 and breechblock 45 are all on a common axis, i.e. they are coaxially arranged. This screw action preloads the sealing of cartridge 11 with a force of about 200 Newtons, sets the axial position of co-volume seal ring 34 to a selected position, and pushes the ignition contacts of the application device against the ignition contacts of cartridge 11 so that electrical contact is established between these ignition contacts.

After an injection process is terminated, a 100 bar residual pressure in cartridge 11 generates a force of about 1600 Newtons on clamp screw 52. Under this mechanical load, the user turns clamp screw 52 to retract breechblock 45 and vent cartridge 11. One of the ends of clamp screw 52 has right hand threads that engage matching threads in receiver ring 55, whereas the opposite end of clamp screw 52 has left hand threads that engage matching threads in breechblock 45. One or more pins in receiver ring 55 engage matching axial slots in breechblock 45, and prevent rotation of breechblock 45 while allowing axial motion thereof. The provision of clamp screw 52 with the above mentioned different threads makes it possible to obtain an axial displacement of breechblock 45 per revolution of clamp screw 52 that is twice as long as the axial displacement that would be obtained if clamp screw 52 had only a single type of thread with the same thread pitch distance. A suitable choice of thread diameter and pitch favorably influences the amount of effort needed for disassembling, respectively assembling application device 41. This is discussed in more detail hereinafter.

A pair of interlock levers 56, 57 consisting each of a latch portion 69 and an arm portion 68 are pivot mounted on a pivot 70 to the receiver ring 55. Interlock levers 56, 57 lie in a plane that includes the symmetry axis of receiver ring 55, and the pivot axes are perpendicular to this plane and symmetrically placed on each side of the symmetry axis of the receiver ring. Interlock levers 56, 57 are spring biased by a bias spring 60 so that the latch portions 69 engage a pair of grooves (not shown) in clamp screw 52, preventing screw rotation. When the shell 43 of pressure chamber 49 is inserted into receiver ring 55, the arm portions 68 of interlock levers 56, 57 slip into a pair of cam grooves 58, 59 in the shell 43 of pressure chamber 49. Cam grooves 58, 59 are shaped to move the arm portions 68 of interlock levers 56, 57 as the shell 43 of pressure chamber 49 is rotated to engage locking lugs 53, so that the latch portions 69 are removed from the clamp screw grooves. The result is that rotation of clamp screw 52 is only possible when the locking lugs 53 are fully engaged with pockets 54.

A second function of interlock levers 56, 57 is to prevent rotation of lugs 53 and disengagement thereof from pockets 54 once clamp screw 52 is rotated from the starting position to clamp cartridge 11 and thereby the closure plug of cartridge 11 and pressure chamber 49 by means of breechblock 45. When clamp screw 52 is rotated, the latch portions 69 of the interlock levers 56, 57 ride on the outside diameter of clamp screw 52, and can no longer enter the clamp screw grooves and rotate about pivots 70. The arm portions 68 of interlock levers 56, 57 are therefore immovable, and bear against the sides of the cam grooves 58, 59 in the shell 43 of pressure chamber 49 and block rotation of locking lugs 53. This ensures that lugs 53 remain fully engaged with pockets 54 during actuation of cartridge 11 and can only be disengaged after clamp screw 52 is returned to the starting position. At this point the latch portions 69 of interlock levers 56, 57 can again drop into the clamp screw grooves, allowing the latches 69 of interlock levers 56, 57 to rotate about the pivots 70.

A third function of interlock levers 56, 57 is to prevent shell 43 of pressure chamber 49 from being inserted if clamp screw 52 is not in the starting position. In this condition the latch portions 69 of the interlock levers 56, 57 ride on the outside diameter of clamp screw 52, displacing the arm portions 68 of the levers so that they do not enter the cam grooves in the shell 43 of pressure chamber 49. This blocks the shell 43 of pressure chamber 49 from entering the receiver ring 55 far enough for the locking lugs 53 to engage pockets 54. The situation in which the shell 43 of pressure chamber 49 is removed and the clamp screw 52 is not in the starting condition is not normal, and indicates damage or tampering. Correction of this anomalous state requires device service or replacement.

By careful selection of the design parameters of clamp screw 52, the required effort to assembly and disassembly application device 41 are approximately equal and this results in greatly improved ease of use.

Frictional torque of clamp screw 52 varies in function of axial load, screw thread diameter, and friction coefficient. Load reaction torque varies in function of axial load and thread pitch. The reaction torque adds to the friction torque in the closing direction (when assembling application device 41), and increases the user effort. Conversely, the reaction torque subtracts from the friction torque in the opening direction (when disassembling application device 41) and assists the user. Since the axial force is about 200 Newtons in the closing direction and about 1600 Newtons in the opening direction, according to the invention the parameters of clamp screw 52 are selected to equalize the opening and closing torque. The following table summarizes the results of a typical design calculation.

| Parameter | Value |
| --- | --- |
| Clamp screw diameter | 8 mm |
| Screw thread friction coefficient | 0.12 |
| Peak closing force | 200 N |
| Peak opening force | 1600 N |
| Equalized opening and closing torque | 20 N-cm |
| Screw pitch (Total of left and right hand clamp screw sections) | 6 mm |

Housing

Figure 4:
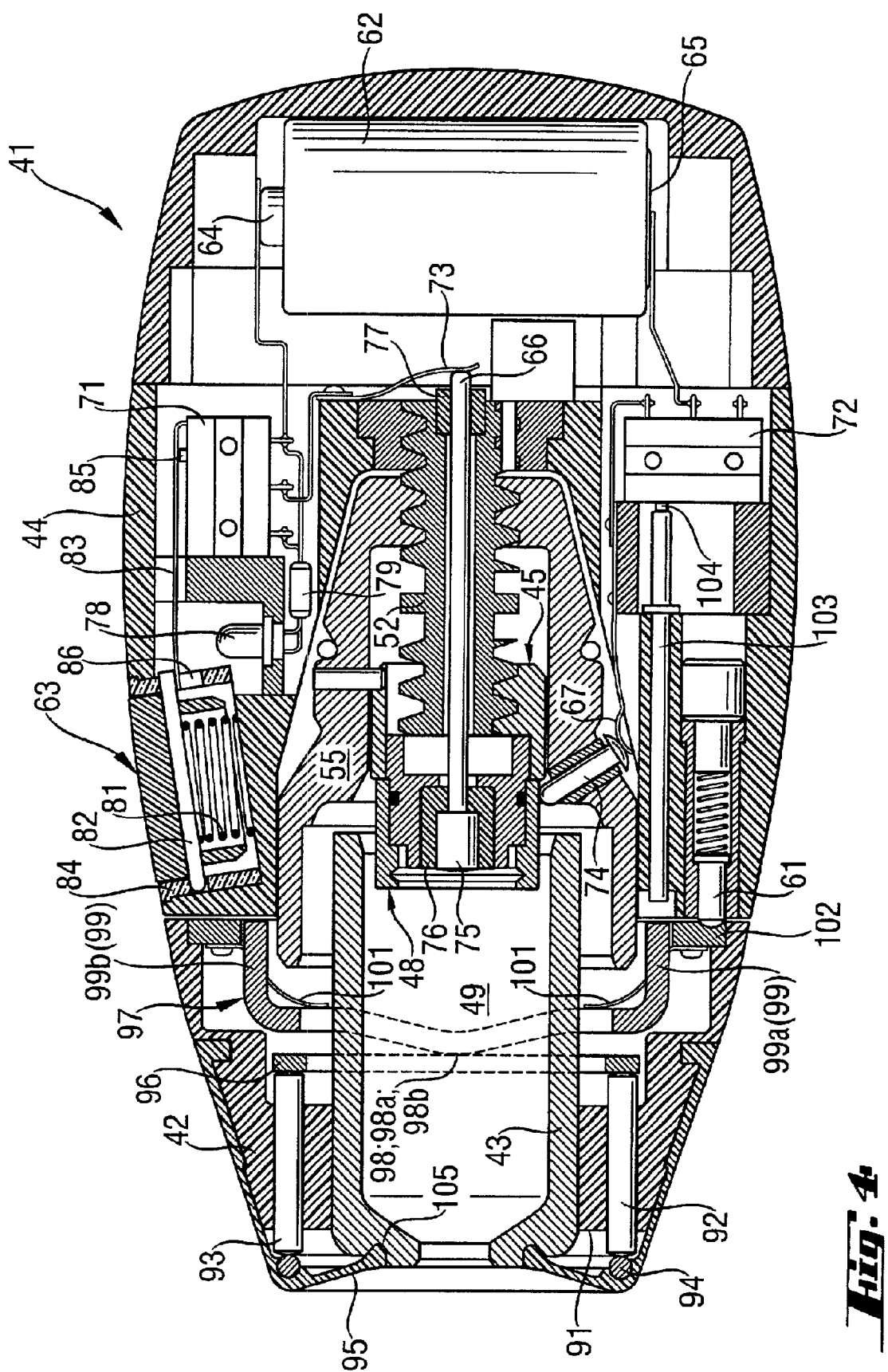
FIG. 4 shows a schematic cross sectional view of a complete application device according to the invention without a medication cartridge inserted thereinto.

FIG. 4 shows a cross section of application device 41 including the housing components. As well as containing the functional components, the housing has important functions of its own. The nose section 42 of the housing is rigidly connected to the shell 43 of pressure chamber 49, and serves as one handle through which the user applies opening and closing torque. The base section 44 of the housing is rigidly connected to clamp screw 52, and serves as the other handle. The base section 44 of the housing rotates relative to the receiver ring 55 and breechblock 45. In combination, the nose section 42 and the base section 44 of the housing also act as visual and tactile indicators, since they have oval profiles that line up when the device is fully closed. Closure of application device 41 is assisted by a spring-loaded pin and detent 61 that latch the application device 41 in the closed position. Additional functions and features of the housing will become evident in the descriptions of other aspects of application device 41.

Figure 8:
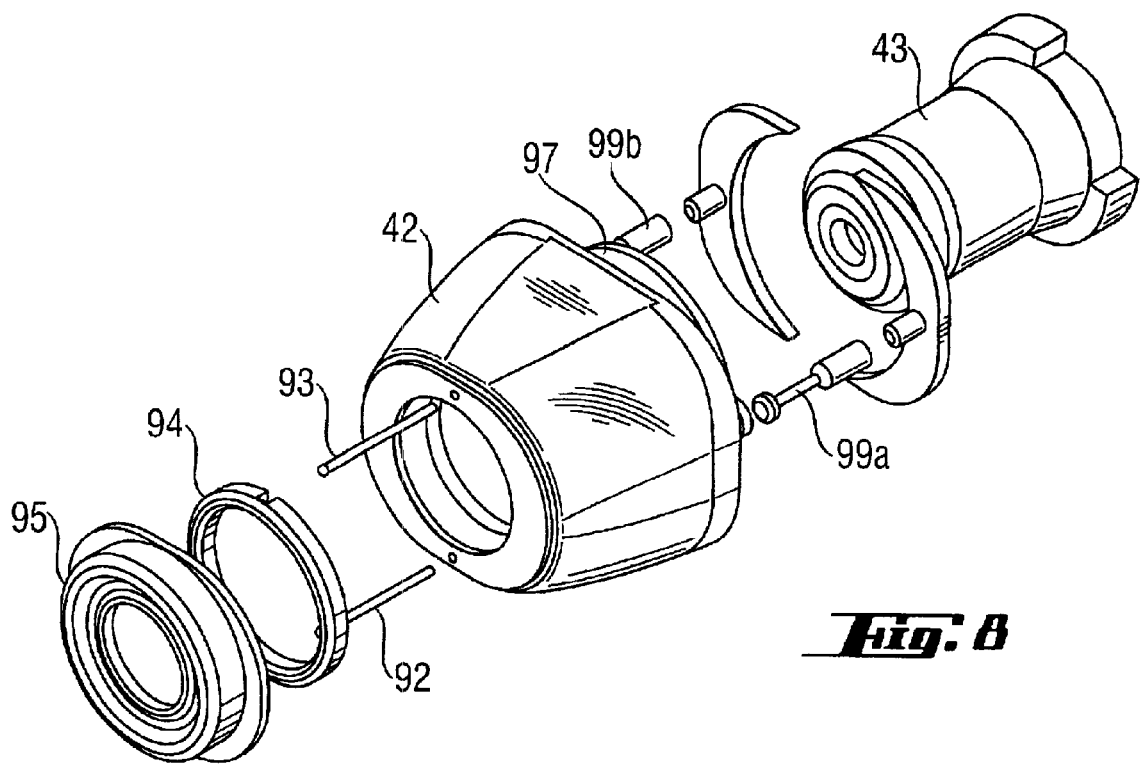
FIG. 8 shows a first exploded view of components of the nose section 42 shown by FIGS. 5–7.
Figure 9:
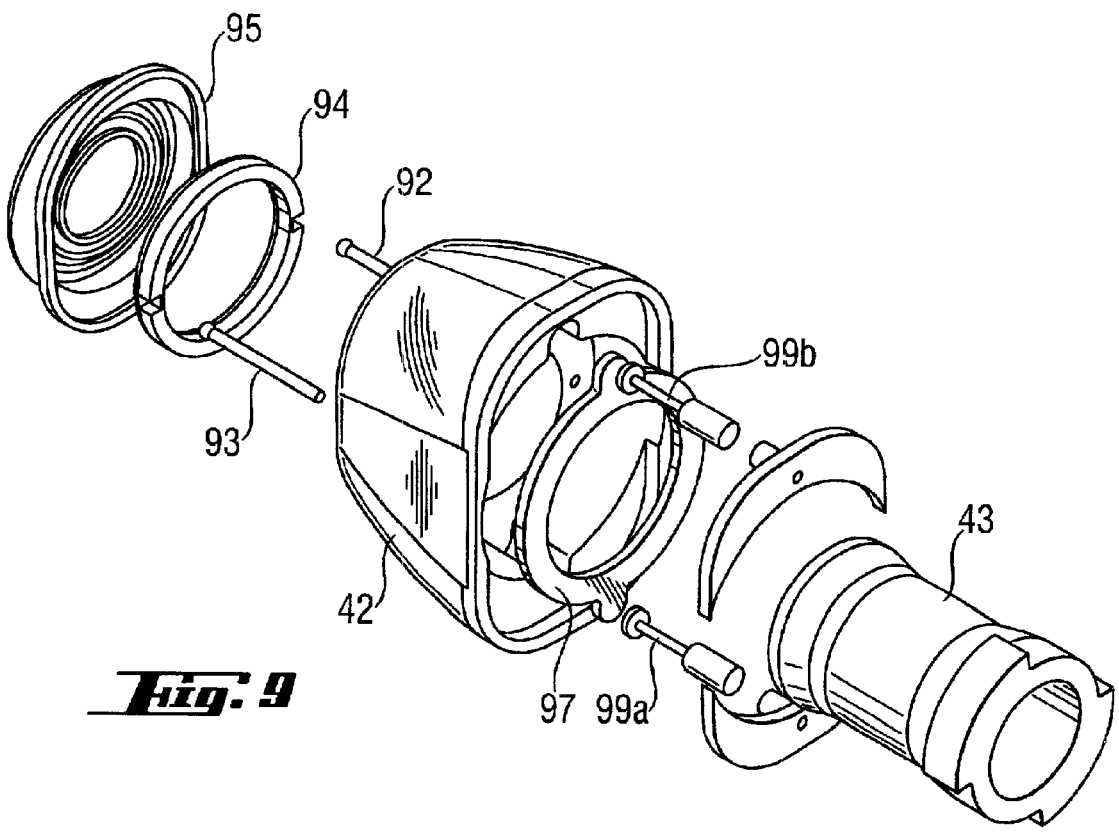
FIG. 9 shows a second exploded view of components of the nose section 42 shown by FIGS. 5–7.

FIGS. 5 to 9 show various views of the nose section 42 and of some of its components. FIG. 5 shows a side view of the nose section 42 of an application device of the kind shown by FIG. 4. FIG. 6 shows a first perspective view of the nose section 42 shown by FIG. 5. FIG. 7 shows a second perspective view of the nose section 42 shown by FIG. 5. FIG. 8 shows a first exploded view of components of the nose section 42 shown by FIGS. 5–7. FIG. 9 shows a second exploded view of components of the nose section 42 shown by FIGS. 5–7.

Electric Ignition System

Figure 10:
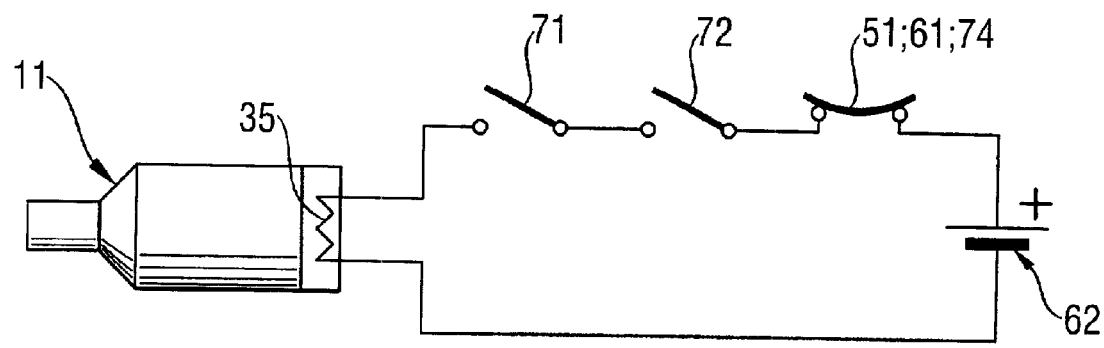
FIG. 10 shows a first schematic representation of the electrical ignition circuit of an application device of the kind shown by FIG. 4.
Figure 11:
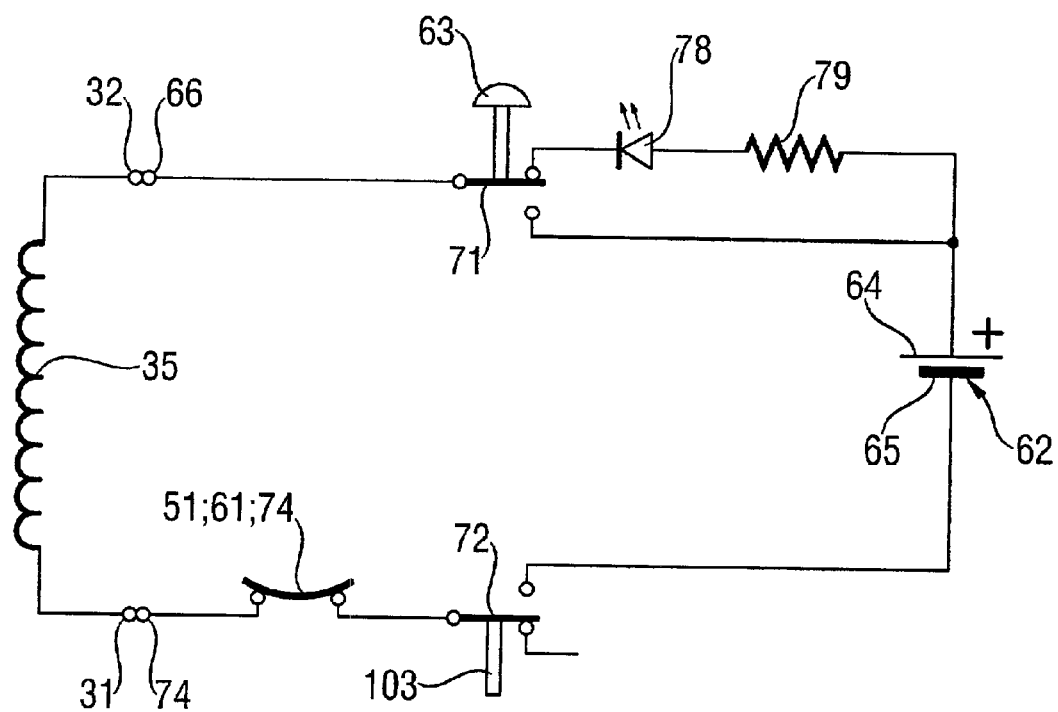
FIG. 11 shows a second schematic representation of the electrical ignition circuit of an application device of the kind shown by FIG. 4.

FIGS. 10 and 11 show schematic representations of the electric ignition system of application device 41.

In its simplest form, the electric ignition system of application device 41 consists of a battery 62, an actuation switch 63 controlled by the user, electrical contacts that engage electrical contacts of cartridge 11, and interconnection conductors. The user loads a fresh cartridge 11 into application device 41, closes and locks this device, removes break-off protective cap 17, presses jet orifice 18 against the skin at the injection site, and then presses push button 63 of the actuation switch. Current passing through an electrically heated wire in the gas generator of cartridge 11 lights the propellant and starts the injection. The invention uses this basic approach, and adds interlock mechanisms to reduce the chance of premature actuation that could cause a hazard or waste an injection cartridge.

The physical configuration of the electric ignition system of this invention is illustrated in FIG. 4. Except as noted, the ignition components are attached to the base section 44 of the housing. Battery 62 is permanently connected by soldering or a similar means, and will normally last the life of application device 41. The positive battery terminal 64 is electrically connected to the input terminal of the normally open actuation microswitch 71, and the negative terminal 65 is connected to the input terminal of the normally open interlock microswitch 72. The output terminal of the actuation microswitch 71 is connected to a conductive spring member 73 that is biased into contact with the central ignition contact pin 66. This contact connection is required since the central ignition contact pin 66 rotates with the receiver ring 55, not with the base section 44 of the housing. The output terminal of the interlock microswitch 72 is connected to a conductive spring member 67 that is biased into contact with the sliding conductive transfer pin 74 in the receiver ring 55. The transfer pin 74 forms a conductive path from the conductive spring member 67 to the co-volume setting ring 48 and then to the breechblock 45. Because the base section 44 of the housing and the receiver ring 55 have rotational and axial relative motion, contact takes place and ignition is possible only when clamp screw 52 is in the predetermined actuation position.

The central ignition contact pin 66 presses against the cartridge center ignition contact 32. The pin head 75 is structurally connected to the sliding breechblock 45, but electrically isolated by an insulating bushing 76. The pin shaft passes through clearance holes in the breechblock 45 and clamp screw 52, and is supported on center by an insulating sleeve bearing 77 to maintain electrical isolation.

The electrically conductive sliding breechblock 45 presses against the outer ignition contact 31 of cartridge 11. As described above, current can only flow to the breechblock 45 when the clamp screw 52 is in the actuation position and the transfer pin 74 makes contact with the conductive spring member 67.

When the interlock microswitch 72 is closed and the clamp screw 52 is in the actuation position, the actuation microswitch 71 is the only remaining barrier to current flow through the ignition contacts and the electrically heated wire 35 in cartridge 11. This results in the battery voltage appearing between the input and outlet terminals of the actuation microswitch 71. This "ready to actuate" condition is visually indicated by a LED 78 connected across the terminals. Actuation then takes place when the user closes the actuation microswitch 71 by pressing push button 63.

A mechanism consisting of a pushbutton 63, coil spring 81, pin lever 82 and flat spring 83 is used to close the actuation microswitch 71 when the user presses the push button 63. This arrangement allows the pushbutton 63 to be positioned so that it is convenient for the user, while the actuation microswitch 71 is positioned where housing space is available. The pushbutton 63 slides in a sleeve 84 in the housing, and is biased out by the coil spring 81. The pin lever 82 serves a dual purpose. First, it is pressed into the pushbutton 63 and extends into openings in the sides of the sleeve 84 to retain the pushbutton 63 in the housing. Second, it acts as a lever that transfers the pushbutton motion to the flat spring 83 that engages the actuation microswitch operating plunger 85. The pin lever 82 pivots in a hole in the side of the sleeve 84 nearest the nose section 42 of the housing of the application device 41, and swings through a slot 86 in the opposite side. The flat spring 83 is anchored at one end, and passes over the microswitch 71 and extends to engage the end of the pin lever 82. When the pin lever 82 swings, it deflects the flat spring 83 towards the actuation microswitch 71 and pushes the actuation plunger 85. The sleeve 84 in the housing is made of translucent plastic that is illuminated by the "ready to actuate" LED 78.

The schematic representation of the electrical ignition system shown by FIG. 10 illustrates the fact that in order that an injection can be performed with application device 41 the following switches have to be closed: switches 71, 72, and switch formed by lock mechanism 51, spring-loaded pin and detent 61 and electrical conductive transfer pin 74. This latter switch is only then closed when the application device 41 is completely assembled, that is when the components contained in nose section 42, in base section 44, and the cartridge 11 are all in the proper position with respect to each other.

The schematic representation of the electrical ignition system shown by FIG. 11 illustrates the state of this system when the application device 41 is completely assembled and all necessary contacts for the ignition are established with exception of switches 71 and 72 which are still open. In this state LED 78 received a current limited by resistor 79. This current is well below the value necessary to cause ignition by electrically heating ignition wire 35, but is large enough to cause light emission by LED 78 and thereby signalize that application device 41 would become ready for performing an injection if and when properly positioned on the injection site.

When the application device 41 reaches a proper position on the injection site, switch 72 is closed by this positioning, and actuation of push button 63 by the user can then cause closure of switch 71. If this happens, the electrical ignition circuit is closed and a sufficiently large current is fed to ignition wire 35 to cause ignition of the propellant in cartridge 11.

Object Sensor/Position Detector

The object sensor or position detector requires the nose section 42 of the housing of the application device 41 to be pressed uniformly against the skin surface at the injection site before actuation is possible/allowed. The object sensor/position detector is illustrated in FIG. 4. The nose section 42 of the housing includes a flat annular surface 91 which surrounds the end of the shell 43 of pressure chamber 49 that protrudes from the housing and the injection nozzle. A pair of diametrically opposed sensor pins 92, 93 slide in holes in the housing, and their ends extend a short distance above the surface in the rest position. The interlock system according to the invention requires that both sensor pins 92, 93 are pushed flush with the annular surface 91 to enable execution of an injection. Sensor pins 92, 93 support a concentric rigid metal sensor ring 94 that is free to pivot at the contact points with the sensor pins 92, 93. This defines the condition that two or more separate points must be pressed to push the sensor ring 94 and both pins 92, 93 flush with the annular surface 91 and enable execution of an injection. If the sensor ring 94 is pressed at any one point around its circumference it will tip, and at most one of the two sensor pins 92, 93 will be pushed flush with the annular surface 91. The annular area, including the sensor ring 94 and sensor pins 92, 93, is covered by a flexible rubber boot 95. The inner edge of the boot 95 is bonded to the shell 43 of the pressure chamber 49 at a bond point 105, and the outer edge of boot 95 fits in a groove in the nose section 42 of the housing. The boot 95 forms a smooth, easily cleaned surface and protects the mechanism. It also retains the sensor ring 94 and holds it in the proper spatial relationship with the sensor pins 92, 93 at the rest position.

The sensor pins 92, 93 push a relay ring 96 inside the nose section 42 of the housing. The relay ring 96 in turn pushes a tilt plate 97. The tilt plate 97 contacts the relay ring 96 with two diametrically opposed raised pivot points 98 (98a respectively 98b), and two diametrically opposed legs 99 (99a respectively 99b) extend towards the base section 44 of the housing. The legs 99 are offset 90 degrees from the pivot points 98, and lie in the same plane as the sensor pins 92, 93. A return spring 101 formed from sheet spring material pushes the tilt plate 97, relay ring 96 and sensor pins 92, 93 towards the nose section 42 of the housing so that the sensor ring 94 is pushed out to the rest position. A cover plate 102 on the surface of the nose section 42 of the housing that abuts the base section 44 of the housing supports the return spring 101 and shields the mechanism. The tilt plate legs 99 pass through holes in the cover plate 102, with their ends flush with the outer surface in the rest position.

When the nose section 42 of the housing is attached to the base section 44 of the housing and the clamp screw 52 is locked, one of the two tilt plate legs 99 is aligned with the interlock push pin 103. This pin contacts the interlock microswitch plunger 104, and closes the interlock microswitch 72 when it is pushed by one of the tilt plate legs 99. The other tilt plate leg contacts the base section 44 of the housing and forms a pivot point. If the sensor ring 94 pushes both sensor pins fully, then the relay ring 96 is pushed uniformly against the two tilt plate pivot points. This causes the tilt plate 97 to rotate around the pivot point formed by the leg in contact with the housing so that the other leg extends, pushes the interlock push pin 103, and closes the interlock microswitch 72. In the event that only one sensor pin 92 or 93 is pushed, the relay ring 96 tilts rather than moving uniformly. The two points on the relay ring 96 that contact the tilt plate 97 pivots move only half the full distance, with the result that the tilt plate leg 99 moves only half the full distance and does not close the interlock switch 72.

This above described object sensor/position detector has a number of useful features. First, it is electromechanical, and does not contain any electronic devices that are sensitive to and whose operation can be affected by spurious signals from electrostatic discharge or other sources of electromagnetic interference. Second, the electric ignition circuit is totally within the base section 44 of the housing, with no connections to the removable nose section 42 of the housing that could compromise reliability. Third, additional safety is provided by the fact that the device must be fully closed and locked to align the tilt plate leg 99 with the interlock push pin 103. Fourth, the structure of the object sensor/position detector is symmetrical, so that the nose section 42 of the housing may be connected to the base section 44 of the housing in either of two positions which are angularly spaced from each other of 180 degrees.

| List of reference numbers | |
|---|---|
| 11 | medication cartridge/cartridge assembly |
| 12 | cartridge shell |
| 13 | nozzle body |
| 14 | flexible container wall |
| 15 | medication reservoir |
| 16 | liquid medication |
| 17 | break-off protective cap |
| 18 | jet orifice |
| 19 | |
| 20 | |
| 21 | envelope |
| 22 | fluid channel |
| 23 | gas generator body |
| 24 | propellant chamber |
| 25 | outlet orifice plate |
| 26 | closure plug/closure plate |
| 27 | gas pressure chamber |
| 28 | annular co-volume |
| 29 | |
| 30 | |
| 31 | ignition contact |
| 32 | ignition contact |
| 33 | internal support |
| 34 | co-volume seal ring |
| 35 | electrically heated wire/ignition wire |
| 36 | |
| 37 | |
| 38 | |
| 39 | |
| 40 | |
| 41 | application device |
| 42 | nose section |
| 43 | shell of pressure chamber |
| 44 | base section |
| 45 | breech block |
| 46 | reduced diameter opening |
| 47 | full diameter opening |
| 48 | co-volume setting ring |
| 40 | pressure chamber |
| 50 | |
| 51 | lock mechanism |
| 52 | clamp screw |
| 53 | male locking lugs |
| 54 | female pockets |
| 55 | receiver ring |
| 56 | interlock lever |
| 57 | interlock lever |
| 58 | cam groove |
| 59 | cam groove |
| 60 | bias spring |
| 61 | spring-loaded pin and detent |
| 62 | battery |
| 63 | push button/actuation button |
| 64 | positive terminal |
| 65 | negative terminal |
| 66 | central ignition contact pin |
| 67 | conductive spring member |
| 68 | arm portion |
| 69 | latch portion |
| 70 | pivot |

-continued

List of reference numbers

| | |
|---|---|
| 71 | actuation micro-switch |
| 72 | interlock micro-switch |
| 73 | electrical conductive spring member |
| 74 | electrical conductive transfer pin |
| 75 | pin head |
| 76 | insulating bushing |
| 77 | insulating sleeve bearing |
| 78 | Light Emitting Diode (LED) |
| 79 | electrical resistance |
| 80 | |
| 81 | coil spring |
| 82 | pin lever |
| 83 | flat spring |
| 84 | sleeve |
| 85 | operating plunger/actuation plunger |
| 86 | slot |
| 87 | |
| 88 | |
| 89 | |
| 90 | |
| 91 | flat annular surface |
| 92 | sensor pin |
| 93 | sensor pin |
| 94 | metal sensor ring |
| 95 | flexible rubber boot |
| 96 | relay ring |
| 97 | tilt plate |
| 98 | pivot point (98a, 98b) |
| 99 | leg (99a, 99b) |
| 100 | |
| 101 | return spring |
| 102 | cover plate |
| 103 | interlock push pin |
| 104 | interlock microswitch plunger |
| 105 | bond point |

Although a preferred embodiment of the invention has been described using specific terms, such description is for illustrative purposes only, and it is to be understood that changes and variations may be made without departing from the spirit or scope of the following claims.

What is claimed is:

1. A reusable application device for a needleless hypodermic injection system for injecting a liquid medication, which application device comprises:

(a) a housing including a first housing section and a second housing section which are adapted to be assembled together by a screwing operation, said first housing section comprising a front part having an injection outlet and a chamber adapted to receive a cartridge containing a medication unit which contains the medication to be injected, a propellant, and an igniter, (b) means for selectively activating said igniter of said cartridge when predetermined conditions are fulfilled, and (c) means providing a visual or audible indication to the user when said predetermined conditions are met and the device is ready for performing an injection.

2. A reusable application device for a needleless hypodermic injection system for injecting a liquid medication contained in a cartridge inserted into said application device, said application device comprising:

a) a housing including a first section and a second section which are adapted to be connected with each other to form a housing assembly, said first housing section comprising a chamber for receiving a cartridge containing a medication unit which contains a liquid medication, said first housing section having a symmetry axis which extends along its length and a front part having an outer contact surface which is adapted to be applied on a skin surface, said contact surface having an opening through which liquid medication ejected from said cartridge can pats and be injected through said skin surface, b) ejection means for causing ejection of said liquid medication contained in said cartridge in order to perform an injection, a first part of said ejection means being contained in said cartridge and a second part of said ejection means being contained in said second housing section, c) assembly detecting means which reach a first predetermined state when said first housing section is properly and completely assembled with said second housing section to form said housing assembly, said assembly detecting means being located within said housing assembly, d) position detecting means which are located in part within said first housing section and in part in said second housing section, said position detecting means reaching a second predetermined state when the following conditions are simultaneously satisfied by the relative position of said housing assembly with respect to said skin surface, d.2) said contact surface of said first section exerts a predetermined pressure on said skin surface, the distribution of said pressure over the area of said contact surface being substantially uniform, and d.3) said symmetry axis of said first section is positioned substantially normal to said skin surface, and e) actuator means for activating said election means, said actuator means being normally disabled and becoming operable only upon being enabled by a combination of predetermined effects provided by said assembly detecting means after they reach said first predetermined state, and said position detecting means when they reach said second predetermined state.

3. A device according to claim 2, wherein said second housing section comprises means which are adapted to cooperate with a corresponding part of said first housing section for clamping with a predetermined preload and for hermetically closing a cartridge inserted into said cartridge receiving chamber.

4. A device according to claim 2, wherein said assembly detecting means exclusively comprise mechanical means.

5. A device according to claim 2, wherein said position detecting means exclusively comprise mechanical and electro-mechanical means, but no electronic means sensitive to electrical noise or other perturbating electrical signals.

6. A device according to claim 2, wherein said position detecting means comprise a first switch adapted to be mechanically actuated by a movable part of said position detecting means to establish an electrical connection when said position detecting means senses application of said front part of said first housing part on said skin surface with a predetermined pressure applied on the skin surface.

7. A device according to claim 2, wherein said first housing part and said second housing part are so shaped, dimensioned and configured that proper and complete assembly thereof is accurately defined and recognizable by visual and tactile inspection.

8. A device according to claim 2, wherein said first housing part and said second housing part are adapted to be assembled together by assembling steps which include a screwing operation.

9. A reusable application device according to claim 2, wherein said housing assembly is so configured and dimensioned that it is adapted to be held and used by a user with only one hand.

10. A reusable application device according to claim 2, which further comprises means providing a visual or audible indication to the user when said actuator device is enabled by said combination of predetermined effects.

11. A reusable application device for a needleless hypodermic injection system for injecting a liquid medication contained in a cartridge inserted into said application device, said cartridge containing a propellant adapted to be ignited by application of electrical energy to two electrical contacts which are part of said cartridge, said application device comprising:

a) a housing including a first section and a second section, each of these sections having a length axis and said first and second housing sections being adapted to be connected with each other to form a housing assembly, said housing assembly being so configured and dimensioned that it is adapted to be held by a user with one hand, b) said first housing section comprising a chamber for receiving a cartridge containing a liquid medication, said first section having an outer contact surface which is adapted to be applied on a skin surface through which an injection is to be applied, c) said second housing section containing electrical means for causing ignition of a propellant contained in a cartridge arranged in said chamber of said first housing section and actuator means for activating said electrical means, and d) position detecting means for detecting whether said contact surface of said first section exerts a predetermined pressure on said skin surface and whether at the same time said length axis of said first section is positioned substantially normal to said skin surface, the distribution of said pressure over the area of said contact surface being substantially uniform, said means for detecting enabling said actuator means when the latter conditions are satisfied.

12. A device according to claim 11, wherein said second housing section comprises means which are adapted to cooperate with a corresponding part of said first housing section for clamping with a predetermined preload and for hermetically closing a cartridge inserted into said cartridge receiving chamber.

13. A reusable application device for a needleless hypodermic injection system for injecting a liquid medication, which application device comprises:

(a) a housing including a first housing section and a second housing section which are adapted to be assembled together by a screwing operation, said first housing section comprising a front part having an injection outlet and a chamber adapted to receive a cartridge containing a medication unit which contains the medication to be injected, a propellant, and an igniter, and (b) means for selectively activating said igniter of said cartridge when predetermined conditions are fulfilled, wherein said means for selectively activating said igniter comprise a purely mechanical object sensor, and a first switch adapted to be mechanically actuated by a movable part of said object sensor to establish an electrical connection when said object sensor senses application of said front part of said first housing part on a body part.

14. A reusable application device for a needleless hypodermic injection system for injecting a liquid medication, which application device comprises:

(a) a housing including a first housing section and a second housing section which are adapted to be assembled together by a screwing operation, said first housing section comprising a front part having an injection outlet and a chamber adapted to receive a cartridge containing a medication unit which contains the medication to be injected, a propellant, and an igniter, and (b) means for selectively activating said igniter of said cartridge when predetermined conditions are fulfilled, wherein at least part of said means for selectively activating said igniter are lodged within said second housing part and comprise an electrical circuit including a battery, said first switch a second switch adapted to be actuated by a user, interconnection conductors, and two electrical terminals which correspond to respective terminals of said igniter, said electrical circuit being so configured that electrical current can flow from the battery to the igniter only when the following conditions are met:

i) said cartridge is properly positioned within said chamber of said first housing part, ii) said first and said second housing part are completely and properly assembled, whereby said two terminals of said electrical circuit contact said respective terminals of said igniter, iii) said first switch is actuated by said object sensor and thereby establishes an electrical connection, and iv) said second switch is actuated by a user.

15. A medication cartridge for a needleless hypodermic injection system for injecting a liquid medication, said cartridge comprising a housing adapted to contain:

(a) a first chamber containing a medication unit configured and dimensioned to store a volume of liquid to be injected, said medication unit having a first region and a second region that are in liquid communication with each other, said first region being deformable and said second region having an injection outlet, and (b) a second chamber containing a propellant, said first chamber being divided by an elastic baffier in two zones, a first zone containing said medication unit and a second zone which is communication with said second chamber, so that upon ignition of the propellant in the second chamber gas generated thereby expands into said second zone of said first chamber, exerts pressure on and deforms said baffier which in turn transfers that pressure to and deforms said deformable first region of said medication unit and thereby causes ejection of said medication through said injection outlet, and (c) means for mechanically setting the volume available within said cartridge for gas said expansion, so that said volume has a selected predetermined size.

16. A medication cartridge according to claim 15, which further comprises an envelope which surrounds said elastic barrier and protects it from direct contact with hot gas generated by ignition of said propellant in said second chamber.

17. A medication cartridge according to claim 16, wherein said envelope also forms a gas seal between said housing and said medication unit containing said liquid medication.

* * * * *

UNITED STATES PATENT AND TRADEMARK OFFICE
CERTIFICATE OF CORRECTION

PATENT NO. : 6,986,754 B2
APPLICATION NO. : 10/101400
DATED : January 17, 2006
INVENTOR(S) : Haar et al.

It is certified that error appears in the above-identified patent and that said Letters Patent is hereby corrected as shown below:

<u>Column 16,</u>
Line 6, "which liquid medication ejected from said cartridge can pats and be injected through said skin surface," should read -- which liquid medication ejected from said cartridge can pass and be injected through said skin surface, --.

<u>Column 18,</u>
Line 44, "said first chamber being divided by an elastic baffier in" should read -- said first chamber being divided by an elastic barrier in --.
Line 50, "pressure on and deforms said baffier which in turn" should read -- pressure on and deforms said barrier which in turn --.

Signed and Sealed this

Twenty-seventh Day of June, 2006

JON W. DUDAS
*Director of the United States Patent and Trademark Office*